United States Patent
Blake et al.

(10) Patent No.: US 6,451,317 B1
(45) Date of Patent: Sep. 17, 2002

(54) **IMMUNOGENIC CONJUGATES COMPRISING A GROUP B MENINGOCOCCAL PORIN AND AN *H INFLUENZAE* POLYSACCHARIDE**

(75) Inventors: Milan S. Blake, Fulton; Francis Michon, Bethesda East; Peter C. Fusco, Burtonsville; Iver Heron, Bethesda, all of MD (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 09/118,180

(22) Filed: Jul. 17, 1998

Related U.S. Application Data

(60) Provisional application No. 60/052,952, filed on Jul. 17, 1997, and provisional application No. 60/057,795, filed on Sep. 8, 1997.

(51) Int. Cl.$^7$ ............................................. A61K 39/385
(52) U.S. Cl. ................................. 424/197.11; 424/184.1; 424/193.1; 424/203.1; 424/249.1; 424/250.1; 424/256.1; 530/350; 530/391.7
(58) Field of Search .......................... 424/184.1, 193.1, 424/197.11, 203.1, 249.1, 250.1, 256.1; 530/350, 391.7

(56) References Cited

U.S. PATENT DOCUMENTS

| | | | |
|---|---|---|---|
| 5,439,808 A | 8/1995 | Blake et al. | 435/69.1 |
| 5,747,287 A | 5/1998 | Blake et al. | 435/69.1 |

FOREIGN PATENT DOCUMENTS

| | | | |
|---|---|---|---|
| EP | 0338265 | * | 10/1989 |
| WO | WO 95/03069 | | 2/1995 |
| WO | WO 95/03413 | | 2/1995 |
| WO | WO 97/28273 | | 8/1997 |

OTHER PUBLICATIONS

Cruse et al. Illustrated Dictionary of Immunology. 1995. pp. 212 and 242.*
Wolff et al. FEMS Microbio. Letters. 1991. 83: 179–186.*
Garner et al. Contrib. Microbiol. Immunol. 1989. 10: 11–17.*
Blake, M.S. and E.C. Gotschlich, "Functional and Immunologic Properties of Pathogenic Neisseria Surface Proteins," in: *Bacterial Outer Membranes as Model Systems*, Inouye, M., ed., John Wiley & Sons, New York, NY, pp. 377–400 (1987).
Butcher, S., et al., "Class–3 porin protein of *Neisseria meningitidis*: cloning and structure of the gene," *Gene* 105:125–128 (1991).
Carbonetti, N.H. and P.F. Sparling, "Molecular cloning and characterization of the structural gene for protein I, the major outer membrane protein of *Neisseria gonorrhoeae*," *Proc. Natl. Acad. Sci. USA* 84:9084–9088 (1987).
Donnelly, J.J., et al., "Immunogenicity of a *Haemophilus influenzae* Polysaccharide–*Neisseria meningitidus* Outer Membrane Protein Complex Conjugate Vaccine," *J. Immunol.* 145:3071–3079 (1990).
Gotschlich, E.C., et al., "Porin protein of *Neisseria gonorrhoeae*: Cloning and gene structure," *Proc. Natl. Acad. Sci. USA* 84:8135–8139 (1987).
Jeanteur, D., et al., "The bacterial porin superfamily: sequence alignment and structure prediction," *Molec. Microbiol.* 5:2153–2164 (1991).
Jennings, H.J. et al., "Unique Intermolecular Bactericidal Epitope Involving the Homosialopolysaccharide Capsule on the Cell Surface of Group B *Neisseria meningitidis* and *Escherichia coli* K1," *J. Immunol.* 142:3585–3591 (1989).
Jennings, H.J. and R.K. Sood, "Synthetic Glycocojugates as Human Vaccines," in:*Neoglycoconjugates: Preparation and Applications*, Lee, Y.C. and R.T. Lee, eds., Academic Press, San Diego, CA, pp. 325–371 (1994).
Liu, M.A., et al., "A vaccine carrier derived from *Neisseria meningitidis* with mitogenic activity for lymphocytes," *Proc. Natl. Acad. Sci. USA* 89:4633–4637 (1992).
Livingston, P.O., et al., "GD3/proteosome vaccines induce consistent IgM antibodies against the ganglioside GD3," *Vaccine* 11:1199–1204 (1993).
Lowell, G.H., et al., "Peptides Bound to Proteosomes via Hydrophobic Feet become Highly Immunogenic without Adjuvants," *J. Experimental Med.* 167:658–663 (1998).
Lowell, G.H., et al., "Proteosome–Lipopeptide Vaccines: Enhancement of Immunogenicity for Malaria CS Peptides," *Science* 240:800–802 (1988).
Lowell, G.H., "Proteosomes, Hydrophobic Anchors, Iscoms, and Liposomes for Improved Presentation of Peptide and Protein Vaccines," in: *New Generation Vaccines*, Woodrow and Lever, eds., Marcel Dekker, Inc., New York, NY, pp. 141–160 (1990).
Lynch, E.C., et al., "Studies of Porins: Spontaneously Transferred from Whole Cells and Reconstituted from Purified Proteins of *Neisseria gonorrhoeae* and *Neisseria meningitidus*," *Biophysical J.* 45:104–107 (1984).
Mauro, A., et al., "Voltage gating of conductance in lipid bilayers induced by porin from outer membrane of *Neisseria gonorrhoeae*," *Proc. Natl. Sci. USA* 85:1071–1075 (1988).
Melancon, J., et al., "Activation of Murine B Lymphocytes by *Neisseria meningitidis* and Isolated Meningococcal Surface Antigens," *Infection and Immunity* 42:471–479 (1983).
Qi, H.L., et al., "Expression of Large Amounts of Neisserial Porin Proteins in *Escherichia coli* and Refolding of the Proteins into Native Trimers," *Infection and Immunity* 62:2432–2439 (1994).
Reuter, G. and R. Schauer, "Determination of Sialic Acids," *Methods in Enzymology* 230:168–199 (1994).

(List continued on next page.)

*Primary Examiner*—Jennifer E. Graser

(57) ABSTRACT

Disclosed is an *H. influenzae* type b polysaccharide-meningococcal outer membrane protein conjugate, pharmaceutical compositions thereof, and the use thereof to induce an immune response to *H. influenzae* in an animal.

9 Claims, 16 Drawing Sheets

OTHER PUBLICATIONS

Sparkes, B.G., "Immunomodulating activity of meningococcal antigens," *Canadien J. Microbiol.* 29:1611–1618 (1983).

Sparkes, B.G., "Dual effect of meningococcal antigens on a T cell dependent immune response," *Canadien J. Microbiol.* 29:1619–1625 (1983).

Ulmer, J.B., et al., "Pore Formation and Mitogenicity in Blood Cells by the Class 2 Protein of *Neisseria meningitidis*," *J. Biol. Chem.* 267:19266–19271 (1992).

Vordemeier, H.M. and W.G. Bessler, "Polyclonal Activation of Murine B Lymphocytes in vitro by *Salmonella typhimurium* Porins," *Immunobiol.* 175:245–251 (1987).

Vordemeier, H.M., et al., "Polyclonal activation of human peripheral blood lymphocytes by bacterial porins and defined porin fragments," *Immunology Letters* 15:121–126 (1987).

Ward, M.J., et al., "Sequence analysis and relationships between meningococcal class 3 serotype proteins and other porins form pathogenic and non–pathogenic Neisseria species,"*FEMS Microbiol. Letters* 94:283–290 (1992).

Wetzler, L. M., et al., "Gonococcal Porin Vaccine Evaluation: Comparison of Por Proteosomes, Liposomes, and Blebs Isolated from rmp Deletion Mutants," *J. Infectious Diseases* 166:551–555 (1992).

White, R.G., "Adjuvant Effect of Microbial Products on the Immune Response," *Ann. Rev. Microbiol.* 30:579–600 (1976).

Young, J.D.–E., et al., "Properties of the major outer membrane protein from *Neisseria gonorrhoeae* incorporated into model lipid membranes," *Proc. Natl. Acad. Sci. USA* 80:3831–3835 (1983).

* cited by examiner

| EXP.# | VACCINE/ADJUVANT | ELISA DAY 0 | ELISA DAY 28 | ELISA DAY 38 | ELISA DAY 49 | ELISA DAY 59 |
|---|---|---|---|---|---|---|
| 3079-1 | Hib-rPorB/Al(OH)$_3$ RD188-141-4 | <50 | 4,150 | 151,550 | 156,550 | 55,850 |
| -2 | | <50 | 13,500 | 60,350 | 45,450 | 28,500 |
| -3 | | <50 | 7,550 | 26,850 | 13,000 | 7,600 |
| -4 | | <50 | <50 | 27,050 | 36,200 | 7,650 |
| -5 | | <50 | <50 | 82,700 | 43,000 | 66,000 |
| -6 | | <50 | 8,650 | 54,550 | 80,000 | 59,350 |
| -7 | | <50 | 615 | 97,500 | 49,650 | 85,250 |
| -8 | | <50 | 40,700 | 120,700 | 65,900 | 71,300 |
| -9 | | <50 | 2,250 | 175,700 | 94,330 | 114,375 |
| GEOMEAN | | 25 | 1,715 | 73,400 | 53,450 | 39,800 |
| 3080-1 | Hib-rPorB RD 188-141-4 | <50 | 208 | 116,350 | 42,450 | 141,650 |
| -2 | | <50 | 147 | 143,450 | 153,100 | 246,000 |
| -3 | | <50 | 2,300 | 31,000 | 33,550 | 20,550 |
| -4 | | <50 | 140 | 13,250 | 8,150 | 2,850 |
| -5 | | <50 | <50 | 30,150 | 41,300 | 37,250 |
| -6 | | <50 | <50 | 7,850 | 7,900 | 4,250 |
| -7 | | <50 | 500 | 116,900 | 67,900 | 15,320 |
| -8 | | <50 | <50 | 20,250 | 32,900 | 31,200 |
| -9 | | <50 | <50 | 57,350 | 38,500 | 31,200 |
| GEOMEAN | | 25 | 100 | 39,250 | 33,250 | 25,650 |

FIG.5A

| EXP.# | VACCINE/ADJUVANT | ELISA DAY 0 | ELISA DAY 28 | ELISA DAY 38 | ELISA DAY 49 | ELISA DAY 59 |
|---|---|---|---|---|---|---|
| 3081-1 | Hib-rPorB/Al(OH)$_3$ RD188-141-7 | <50 | 300 | 38,100 | 20,350 | 5,900 |
| -2 | | <50 | 140 | 42,900 | 16,050 | 1,250 |
| -3 | | <50 | 24,500 | 135,050 | 107,450 | 32,800 |
| -4 | | <50 | 700 | 63,100 | 44,050 | 47,050 |
| -5 | | <50 | 2,050 | 94,750 | 40,750 | 136,900 |
| -6 | | <50 | <50 | <50 | <50 | 600 |
| -7 | | <50 | 2,350 | 148,800 | 82,250 | 132,550 |
| -8 | | <50 | 58,100 | 28,900 | 21,750 | 46,050 |
| -9 | | <50 | 1,050 | 20,150 | 15,450 | 6,650 |
| GEOMEAN | | 25 | 1,200 | 24,200 | 15,200 | 15,000 |
| 3082-1 | Hib-rPorB RD 188-141-7 | <50 | <50 | 54,600 | 16,350 | 33,250 |
| -2 | | <50 | 700 | 80,700 | 66,850 | 46,450 |
| -3 | | <50 | <50 | 27,350 | 18,200 | 28,750 |
| -4 | | <50 | 2,750 | 242,150 | 102,600 | 144,300 |
| -5 | | <50 | 1,350 | 171,050 | 55,120 | 43,650 |
| -6 | | <50 | <50 | 7,100 | 2,300 | 11,200 |
| -7 | | <50 | <50 | 19,500 | 9,500 | 38,350 |
| -8 | | <50 | 500 | 68,100 | 27,200 | 36,800 |
| -9 | | <50 | <50 | 78,500 | 32,300 | 85,000 |
| GEOMEAN | | 25 | 130 | 53,700 | 23,450 | 41,650 |

FIG.5B

| EXP.# | VACCINE/ADJUVANT | ELISA DAY 0 | ELISA DAY 28 | ELISA DAY 38 | ELISA DAY 49 | ELISA DAY 59 |
|---|---|---|---|---|---|---|
| 3083-1 | Hib-rPorB/Al(OH)$_3$ RD188-143-4 | <50 | 16,550 | 25,900 | 9,330 | 47,000 |
| -2 | | <50 | 1,650 | 137,700 | 173,800 | 110,750 |
| -3 | | <50 | 17,150 | 102,850 | 38,100 | 36,400 |
| -4 | | <50 | 3,550 | 3,050 | 2,150 | 4,300 |
| -5 | | <50 | <50 | 39,620 | 22,950 | 81,500 |
| -6 | | <50 | <50 | 6,050 | 3,330 | 1,350 |
| -7 | | <50 | <50 | 600 | <20 | 700 |
| -8 | | <50 | <50 | 21,650 | 13,700 | 4,600 |
| -9 | | <50 | 500 | 61,150 | 23,850 | 17,400 |
| GEOMEAN | | 25 | | 18,150 | 6,850 | 12,000 |
| 3084-1 | Hib-rPorB RD 188-143-4 | <50 | <50 | 37,000 | 160 | 34,750 |
| -2 | | <50 | 870 | 449,750 | 545,850 | 462,400 |
| -3 | | <50 | 550 | 38,500 | 11,220 | 10,000 |
| -4 | | <50 | <50 | 27,650 | 9,250 | 9,450 |
| -5 | | <50 | 430 | 25,250 | 52,650 | 13,640 |
| -6 | | <50 | <50 | 67,000 | 3,200 | 37,500 |
| -7 | | <50 | 280 | 14,600 | 65,570 | 55,450 |
| -8 | | <50 | <50 | 3,550 | 18,250 | 6,700 |
| -9 | | <50 | 130 | 12,050 | 22,400 | 26,450 |
| GEOMEAN | | 25 | 110 | 29,850 | 15,100 | 27,000 |

FIG. 5C

| EXP.# | VACCINE/ADJUVANT | ELISA DAY 0 | ELISA DAY 28 | ELISA DAY 38 | ELISA DAY 49 | ELISA DAY 59 |
|---|---|---|---|---|---|---|
| 3085-1 | Hib-rPorB/Al(OH)$_3$ RD188-143-6 | <50 | <50 | 11,450 | 12,700 | 84,000 |
| -2 | | <50 | 1,200 | 10,250 | 27,050 | 10,650 |
| -3 | | <50 | 1,200 | 115,050 | 108,450 | 44,250 |
| -4 | | <50 | 1,240 | 7,350 | 8,250 | 4,300 |
| -5 | | <50 | 40,450 | 66,550 | 37,050 | 39,550 |
| -6 | | <50 | 200 | 114,050 | 47,950 | 27,550 |
| -7 | | <50 | 6,550 | 9,400 | 4,400 | 11,300 |
| -8 | | <50 | 13,450 | 108,500 | 83,850 | 110,350 |
| -9 | | <50 | 6,300 | 128,400 | 101,050 | 73,850 |
| GEOMEAN | | 25 | 800 | 35,900 | 30,100 | 29,550 |
| 3086-1 | Hib-rPorB RD 188-143-6 | <50 | 330 | 84,250 | 82,400 | 190,200 |
| -2 | | <50 | 230 | 13,500 | 2,850 | 10,100 |
| -3 | | <50 | 580 | 11,050 | 1,910 | 8,400 |
| -4 | | <50 | 400 | 100,250 | 47,200 | 46,500 |
| -5 | | <50 | <50 | 19,000 | 7,300 | 2,100 |
| -6 | | <50 | <50 | 10,150 | 4,250 | 2,700 |
| -7 | | <50 | <50 | 700 | 1,050 | 177,000 |
| -8 | | <50 | <50 | 9,500 | 2,900 | 17,600 |
| -9 | | <50 | <50 | 43,850 | 33,500 | 22,900 |
| GEOMEAN | | 25 | 82 | 16,050 | 7,400 | 18,900 |

FIG.5D

| EXP.# | VACCINE/ADJUVANT | ELISA DAY 0 | ELISA DAY 28 | ELISA DAY 38 | ELISA DAY 49 | ELISA DAY 59 |
|---|---|---|---|---|---|---|
| 3087-1 | Hib-TT/Al(OH)$_3$ TC 27 | <50 | <50 | 650 | 10,150 | 450 |
| -2 | | <50 | 7,200 | 74,250 | 44,200 | 49,850 |
| -3 | | <50 | 350 | 5,100 | 1,850 | 2,100 |
| -4 | | <50 | 1,500 | NO SERUM | NO SERUM | NO SERUM |
| -5 | | <50 | <20 | 400 | <50 | <50 |
| -6 | | <50 | 400 | 10,850 | 8,650 | 4,600 |
| -7 | | <50 | 550 | 29,150 | 18,300 | 74,800 |
| -8 | | <50 | <20 | 5,250 | 4,050 | 35,650 |
| -9 | | <50 | 2,300 | 30,300 | 21,450 | 16,050 |
| GEOMEAN | | 25 | 250 | 6,900 | 4,800 | 4,700 |
| 3088-1 | Hib-TT TC 27 | <50 | <20 | 1,000 | 810 | 1,050 |
| -2 | | <50 | 235 | 9,650 | 6,950 | 2,250 |
| -3 | | <50 | 1,450 | 78,800 | 40,900 | 40,200 |
| -4 | | <50 | 1,200 | 156,700 | 119,750 | 56,750 |
| -5 | | <50 | <50 | 4,350 | <50 | <50 |
| -6 | | <50 | <50 | 400 | 38,400 | <100 |
| -7 | | <50 | 324 | 88,800 | 19,200 | 12,600 |
| -8 | | <50 | 212 | 27,000 | 15,300 | 9,550 |
| -9 | | <50 | <50 | 1,050 | 950 | 1,150 |
| GEOMEAN | | 25 | 118 | 9,300 | 5,800 | 2,150 |

FIG.5E

| EXP.# | VACCINE/ADJUVANT | ELISA DAY 0 | ELISA DAY 28 | ELISA DAY 38 | ELISA DAY 49 | ELISA DAY 59 |
|---|---|---|---|---|---|---|
| 3089-1 | Hib-TT/Al(OH)$_3$ TC 21 | <50 | 950 | 1,000 | 1,800 | 1,300 |
| -2 | | <50 | 775 | 7,900 | 6,110 | 5,600 |
| -3 | | <50 | 1,250 | 11,500 | 13,250 | 31,000 |
| -4 | | <50 | 2,050 | 6,200 | 6,850 | 12,600 |
| -5 | | <50 | 22,050 | 28,000 | 4,050 | 4,400 |
| -6 | | <50 | <50 | 5,200 | 1,400 | 2,000 |
| -7 | | <50 | <50 | 49,900 | 28,400 | 63,950 |
| -8 | | <50 | 9,700 | 1,750 | 34,150 | 62,100 |
| -9 | | <50 | 1,120 | 4,450 | 1,500 | 5,150 |
| GEOMEAN | | 25 | 850 | 6,800 | 5,850 | 9,300 |
| 3090-1 | Hib-TT TC 21 | <50 | <50 | 150 | 150 | 500 |
| -2 | | <50 | 1,010 | 91,200 | 51,500 | 35,950 |
| -3 | | <50 | <50 | 4,650 | 1,750 | 3,600 |
| -4 | | <50 | <50 | 5,500 | 5,200 | 2,600 |
| -5 | | <50 | <50 | 1,850 | 950 | 550 |
| -6 | | <50 | <50 | 8,550 | 36,850 | 6,600 |
| -7 | | <50 | <50 | 350 | <50 | 190 |
| -8 | | <50 | 865 | 64,750 | 34,000 | 26,250 |
| -9 | | <50 | <50 | 3,900 | 6,310 | 2,800 |
| GEOMEAN | | 25 | 62 | 4,300 | 2,850 | 2,750 |

FIG.5F

| EXP.# | VACCINE/ADJUVANT | ELISA DAY 0 | ELISA DAY 28 | ELISA DAY 38 | ELISA DAY 49 | ELISA DAY 59 |
|---|---|---|---|---|---|---|
| 3091-1 | Hib-CRM Lederle MO35PE | <50 | <50 | <50 | <50 | 100 |
| -2 | | <50 | <50 | <50 | <50 | 12,350 |
| -3 | | <50 | 1,600 | 180,000 | 44,300 | 107,100 |
| -4 | | <50 | 1,600 | 16,200 | 286,300 | 199,150 |
| -5 | | <50 | 600 | 319,150 | 8,500 | 2,750 |
| -6 | | <50 | <50 | 10,000 | 1,200 | 1,750 |
| -7 | | <50 | <50 | 3,500 | 600 | 1,000 |
| -8 | | <50 | <50 | 3,650 | 1,050 | 8,050 |
| -9 | | <50 | <50 | <50 | <50 | 375 |
| GEOMEAN | | 25 | 90 | 2,300 | 1,030 | 4,200 |
| 3092-1 | Hib-rP2/Al(OH)$_3$ RD 111-187 | <50 | 830 | 5,000 | 4,200 | 2,050 |
| -2 | | <50 | <50 | 450 | 450 | 1,000 |
| -3 | | <50 | 250 | 2,700 | 2,750 | 3,650 |
| -4 | | <50 | 320 | 89,250 | 85,950 | 29,300 |
| -5 | | <50 | 400 | 75,900 | 9,100 | 8,800 |
| -6 | | <50 | <50 | 9,700 | 5,050 | 10,700 |
| -7 | | <50 | 7,300 | 75,850 | 63,050 | 39,250 |
| -8 | | <50 | <50 | 2,900 | 800 | 1,250 |
| -9 | | <50 | 200 | 6,500 | 5,900 | 8,800 |
| GEOMEAN | | 25 | 200 | 9,400 | 5,700 | 5,900 |
| 3093-1 | Hib-rP2 RD 111-187 | <50 | 4,000 | 196,850 | 351,500 | DEAD |
| -2 | | <50 | <50 | 12,300 | 3,850 | 9,300 |
| -3 | | <50 | <50 | 4,100 | 2,600 | 1,650 |
| -4 | | <50 | 450 | 14,700 | 6,100 | 1,000 |
| -5 | | <50 | 180 | 24,000 | 13,350 | 1,300 |
| -6 | | <50 | <50 | 16,500 | 8,700 | 1,100 |
| -7 | | <50 | <50 | 4,300 | 1,900 | 1,800 |
| -8 | | <50 | <50 | 2,900 | 2,050 | 32,400 |
| -9 | | <50 | 850 | 34,150 | 23,550 | 18,500 |
| | | 25 | 116 | 14,250 | 8,500 | 3,500 |

| EXP.# | VACCINE/ADJUVANT | ELISA DAY 0 | ELISA DAY 28 | ELISA DAY 38 | ELISA DAY 49 | ELISA DAY 59 |
|---|---|---|---|---|---|---|
| \multicolumn{7}{c}{CONTINUED FROM FIG.5G} | | | | | | |
| GEOMEAN | | 25 | 116 | 14,250 | 8,500 | 3,500 |
| 3094-1 | Hib-rP2 RD 75-41 | <50 | <50 | 950 | 450 | 1,250 |
| -2 | | <50 | <50 | <50 | <50 | 350 |
| -3 | | <50 | <50 | 1,850 | 950 | 2,450 |
| -4 | | <50 | 1,250 | 114,400 | 9,850 | 62,200 |
| -5 | | <50 | <50 | 4,600 | 250 | 1,800 |
| GEOMEAN | | 25 | 55 | 1,875 | 500 | 2,600 |

FIG.5H

| CONJUGATE VACCINE (ADJUVANT) | GEOMETRIC MEAN TITER (STANDARD ERROR) | | | RESPONDERS*/TOTAL | | |
| --- | --- | --- | --- | --- | --- | --- |
| | 1ST DOSE | 2ND DOSE | 3RD DOSE | 1ST DOSE | 2ND DOSE | 3RD DOSE |
| Hib-rPorB-1 | 110 (63-180) | 39,000 (28,000-55,000) | 26,000 (16,000-41,000) | 5/9 | 9/9 | 9/9 |
| Hib-rPoB-1 (ALUM) | 1,700 (710-4,200) | 73,000 (58,000-92,000) | 40,000 (28,000-56,000) | 7/9 | 9/9 | 9/9 |
| Hib-rPorB-2 | 130 (67-260) | 54,000 (37,000-77,000) | 42,000 (33,000-53,000) | 7/9 | 9/9 | 9/9 |
| Hib-rPorB-2 (ALUM) | 1,200 (540-2,700) | 24,000 (10,000-59,000) | 15,000 (7,800-29,000) | 8/9 | 8/9 | 9/9 |
| Hib-TT | 56 (33-95) | 4,300 (2,100-8,700) | 2,700 (1,500-4,900) | 2/9 | 9/9 | 9/9 |
| Hib-TT (ALUM) | 870 (400-1,900) | 6,800 (4,500-10,000) | 9,300 (5,800-15,000) | 7/9 | 9/9 | 9/9 |
| HbOC | 90 (47-170) | 2,300 (670-8,000) | 4,200 (1,800-9,600) | 3/9 | 6/9 | 9/9 |

FIG.6B

IMMUNOGENIC CONJUGATES COMPRISING A GROUP B MENINGOCOCCAL PORIN AND AN *H INFLUENZAE* POLYSACCHARIDE

This application claims priority to U.S. Provisional Application No. 60/052,952, filed Jul. 17, 1997 and to U.S. Provisional Application No. 60/057,795, filed Sep. 8, 1997.

BACKGROUND OF THE INVENTION

1. Field of the Invention

The present invention is in the field of vaccines useful for raising an immune response in an animal. In particular, the invention relates to *H. influenzae* polysaccharide-*N. meningitidis* outer membrane protein conjugates, pharmaceutical compositions and the use thereof.

2. Background Information

*Haemophilus influenzae* are small, pleomorphic, Gram-negative coccobacilli. Isolates are classified into six antigenically distinct capsular types (a–f) and nonencapsulated, nontypable strains. *Haemophilus influenzae* can cause meningitis, otitis media, sinusitis, epiglottitis, septic arthritis, occult febrile bacteremia, cellulitis, pneumonia, and empyema; occasionally this organism causes neonatal meningitis and septicemia. Other *H. influenzae* infections include purulent pericarditis, endocarditis, conjunctivitis, osteomyelitis, peritonitis, epididymo-orchitis, glossitis, uvulitis, and septic thrombophlebitis. Most cases of invasive diseases in children before the introduction of *H. influenzae* type b (Hib) conjugate vaccination were caused by type b. Nonencapsulated organisms can cause invasive disease in newborns. Nonencapsulated strains cause upper respiratory tract infection, including otitis media, sinusitis, and bronchitis, and may cause pneumonia.

The source of the organism is the upper respiratory tract of humans. The mode of transmission is presumably person to person, by direct contact, or through inhalation of droplets of respiratory tract secretions containing the organism. Asymptomatic colonization by nonencapsulated strains is frequent; organisms are recovered from the throat of 60% to 90% of children. Colonization by type b organisms, however, is infrequent, ranging from 2% to 5% of children in the pre-vaccine era, and appears to be even less frequent with widespread Hib conjugate vaccination. The exact period of communicability is unknown but may be for as long as the organism is present in the upper respiratory tract.

Before the introduction of effective vaccines, Hib was the most common cause of bacterial meningitis in children in the United States and in many other countries. Meningitis and other invasive infections were most common in children 3 months to 3 years of age and approximately half of the cases occurred in infants younger than 12 months. The age-specific incidence of invasive type b disease in different populations in countries has varied; the proportion of disease in infants younger than 12 months tends to be greatest in populations with the highest total incidence, resulting in a lower median age of cases. In contrast to meningitis and most other invasive Hib diseases, epiglottitis is rare in infants younger than 12 months; its peak occurrence in the pre-vaccine era was 2 to 4 years of age. Epiglottitis also can occur in older, unvaccinated children and adults.

Invasive disease has been more frequent in boys, African-Americans, Alaskan Eskimos, Apache and Navajo Indians, child care center attendees, children living in overcrowded conditions and children who were not breast-fed. Unimmunized children, particularly those younger than 4 years who are in prolonged, close contact (such as in a household) with a child with invasive Hib disease, are at an increased risk for serious infection from this organism. Other factors predisposing to invasive disease include sickle cell disease, asplenia, HIV infection, certain immunodeficiency syndromes, and malignancies. Infants younger than 1 year with documented invasive infection are at an approximate 1% risk of recurrence, if not subsequently vaccinated.

Since 1988 when Hib conjugate vaccines were introduced, the incidence of invasive Hib disease has declined by 95% in infants and young children and the incidence of invasive infections caused by other encapsulated types is now similar to that caused by type b. As a result of this success, the U.S. Public Health Service has targeted Hib disease in children younger than 5 years for elimination in this country. Invasive Hib disease occurs now in this country primarily in under vaccinated children and among infants too young to have completed the primary series of vaccinations.

Four Hib conjugate vaccines have been licensed in the United States. These vaccines consist of the Hib capsular polysaccharide (ie, polyribosylribotol phosphate (PRP) or PRP oligomers) covalently linked to a carrier protein directly or via an intervening spacer molecule. Protective antibodies are directed against PRP. Conjugate vaccines differ in composition and immunogenicity and, as a result, recommendations for their use differ. For example, PRP-D is recommended only for children 12 months of age and older, whereas the other three vaccines, HbOC, PRP-T, and PRP-OMP, are recommended for infants beginning at 2 months of age.

Adjuvants are substances that augment the immune response to antigens and, therefore, have been used in many vaccines and vaccine candidates. The immune stimulatory effect of adjuvants is not antigen specific, as they boost immune responses towards many different types of antigens. The only adjuvants currently approved for human use by the FDA are aluminum salts, but many adjuvants used in animal vaccinations and in newer vaccine candidates are microbial in origin (61) e.g. Freund's adjuvant, *Corynebacterium parvum*, muramyl dipetide, tetanus toxoid, etc. The mechanisms for the immunopotentiating ability of microbial substances are unknown.

The major outer membrane proteins of the pathogenic Neisseria (*Neisseria gonorrhoeae* and *Neisseria meningitidis*) have been investigated for adjuvant potential (36,37,39,40,60) and for the mechanism behind their immunopotentiating ability. The proteins of interest are protein IA (PIA) and protein IB (PIB) from the gonococcus and class 1, 2 or 3 proteins from the meningococcus (C1, C2 and C3 respectively) (4). They all function as porins (41,43,62), have significant amino acid sequence homology amongst each other (6,7,21,59) and are considered to be part of the gram negative porin superfamily (26).

Neisserial porins, when complexed non-covalently with malarial peptides, were shown to enhance the antibody response to these peptides as compared to when the peptides were used as an immunogen alone or covalently linked to other proteins (39,40). In addition, peptides derived from Group A streptococcus (38), influenza virus hemagglutinin (38), or *Trypanosome bruceii* (40) were shown to be more immunogenic in mice when incorporated into complexes containing Neisserial porins as compared to when the mice were immunized with peptides alone. Meningococcal outer membrane vesicles (OMV), mainly consisting of the class 2 protein, were used as a carrier to boost the immune response towards the *H. influenzae* polysaccharide capsule in the recently licensed *H. influenzae* type b vaccine developed by Merck (10). Furthermore, Livingston has explored the use of purified Neisserial porins as adjuvants in anti-melanoma vaccines. Melanoma cells express much higher levels of the human gangliosides GM2 or GD3 on their surface as compared to normal melanocytes. To augment the immune response to GM2 and GD3, and possibly induce tumor immunity in melanoma patients, GM2 and GD3 were noncovalently associated with purified Neisserial porins and volunteers with malignant melanoma were immunized with these vaccine constructs. Anti-GM2 or anti-GD3 antibody responses were greatly enhanced in patients immunized with porin/GM2 or porin/GD3 complexes as compared to patients immunized with these gangliosides alone or complexed with BCG (36,37). In addition, the tumor burden in patients immunized with porin/GM2 decreased significantly (personal communication, P. Livingston).

The mechanisms by which the Neisserial porins act as adjuvants are unknown. The group from Merck (10,35,56), who developed the Haemophilus polysaccharide capsule—meningococcal OMV conjugate vaccine, thought that it might be due to direct T cell stimulation by the class 2 protein. They initially demonstrated that the class 2 protein could directly stimulate T lymphocytes and, therefore, they renamed the class 2 protein as the Meningococcal Immune Enhancing Protein (MIEP) (35). However, it was later shown that only denatured class 2 protein at high concentrations (>50 µg) could stimulate T cells, whereas the native protein had no such effect (56). Furthermore, since the majority of the Neisserial porins are in their native configuration when used as a vaccine candidate or adjuvant, the likelihood that non-specific T cell stimulation by denatured porins accounts for their immunopotentiating ability is low.

Over the last few years, details regarding the interaction between T and B lymphocytes required for antigen recognition, lymphocyte stimulation and antibody production have been elucidated. In the current model of T lymphocyte stimulation, two sets of signals between the antigen presenting cell (APC) and the T lymphocyte have been shown to be required (24,25,51). The first signal (signal 1) is delivered via the interaction of the major histocompatibility (MHC) complex on antigenpresenting cells (e.g. B lymphocytes, dendritic cells, macrophages, etc.) and the T cell receptor on T lymphocytes. The groove on the MHC complex is usually occupied by an oligopeptide derived from processed antigens (T cell epitope). The specificity of the reaction is conferred by signal 1. The second or costimulatory signal (signal 2) is delivered by the binding of two sets of counter-receptors during the interaction between the B and T lymphocytes (FIG. 1). The activated T lymphocytes then release cytokines which in turn stimulate the effector cells, for example, causing B lymphocytes to become antibody producing cells. The induction of costimulation by the interaction of these counter-receptors has been shown to be important in tumor immunity. (1,3,8,11,51,55), the prevention of tolerance (19,45,54), and for cytotoxic lymphocyte activity (1).

The T lymphocyte counter-receptors are CD28 and CTLA-4. They are both members of the immunoglobulin superfamily (9). CD28 is present on resting and activated T cells (1,8,27,30,32,34,46), while CTLA-4 is only expressed on activated T cells (17,23,31,33,51). The level of CD28 on activated T cells is 20×higher than CTLA-4 but the affinity of CD28 for its B cell counter-receptor is much lower (31,33). The B lymphocyte counter-receptors are B7 (14, 20,32,48,49) and the more recently discovered B7-2(2,12, 13,16,24). B7 and B7-2 are members of the immunoglobulin superfamily (13–15) and are only present on activated B lymphocytes (14). Several lines of evidence demonstrate the relationship of the newer ligand, B7-2, to T lymphocyte costimulation; 1) CTLA-4 binding to activated B cells is only partially inhibited by an anti-B7 monoclonal antibody (mAb) (24), 2) lymphocytes derived from mice deficient in B7 expression can still costimulate T cells (12,13), 3) transfectants expressing B7-2 alone can costimulate T cells (13,16), and 4) a mAb specific for B7-2 can inhibit T lymphocyte costimulation by B cells (24) or B7-2 transfectants (13). The significance of the initially described B7 antigen as a costimulation counter-receptor is controversial because the expression of B7-2 occurs earlier than the expression of B7 and there is more B7-2 present on the surface of activated B lymphocytes than B7 (24). A schematic representation of T lymphocyte costimulation and the costimulatory counter-receptors is illustrated in FIG. 1.

There is preliminary evidence presented by various investigators that microbial products can stimulate B lymphocytes. Liu et al. have demonstrated that lipopolysaccharide (LPS), mitogenic influenza virus, and an antigen that mimics viral infection (polyinosinic-polycytidylic acid), all stimulate B lymphocytes, which in turn costimulate T lymphocytes (25). Vordermeier has demonstrated that purified *Salmonella typhi* porins (free of LPS) are potent B cell stimulators, but have minimal effect on T lymphocytes (57,58). In addition, meningococcal outer membrane preparations, mainly consisting of the meningococcal porins act as B cell mitogens and do not stimulate T lymphocytes (44,52,53). This evidence suggests that Neisserial porins, and possibly other gram-negative porins, might be able to stimulate B lymphocytes and increase B7-2 expression. The increased expression of B7-2 can mediate T lymphocyte costimulation and this could be a mechanism by which porins enhance the immune response to other antigens, such as the PRP polysaccharide presented here.

BRIEF SUMMARY OF THE INVENTION

The present invention relates to an *H. influenzae* type b (Hib) polysaccharide-substantially pure, refolded meningococcal outer membrane protein (rPorB) conjugate.

The present invention also relates to a method of preparing an Hib polysaccharide-rPorB conjugate, comprising (a) obtaining an Hib polysaccharide;

(b) oxidizing or selectively hydrolyzing said polysaccharide to generate aldehyde groups;

(c) obtaining a rPorB; and (d) conjugating the polysaccharide containing aldehyde groups to the rPorB by reductive amination.

The present invention also relate to the conjugates obtained according to the methods of the invention. Optionally, the conjugates of the present invention may be combined with DTaP (diphtheria, tetanus, acellular pertussis vaccine).

The present invention also relates to pharmaceutical compositions comprising the conjugates of the invention, optionally comprising DTaP, and a pharmaceutically acceptable carrier.

The present invention also relates to a method of inducing an immune response in an animal to *H. influenzae*, comprising administering the conjugates of the invention to the animal in an amount effective to induce said immune response.

The invention relates in part to the surprising discovery that the Hib-rPorB conjugates of the invention induce substantially greater immune responses in animals compared to when tetanus toxoid and the recombinantly produced outer membrane P2 protein from *H. influenzae* is used as the antigenic protein. Substantially greater immunogenic responses were also obtained compared to the Hib-CRM conjugate which is commercially available from Lederle Laboratories, Division of American Cyanamide Company, Pearl River, N.Y. $CRM_{197}$ is a site mutant, non-toxic variant of diphtheria toxin isolated from cultures of *Cornebacterium diphtheriae* C7(β0197). Seid, R. C. Jr. et al., *Glycoconj. J.* 6: 489–498(1989).

Furthermore, the conjugate of the present invention is especially useful in compositions also comprising DTAP, as immunologic interactions between the components, as well as epitopic suppression, is observed with conventional carrier proteins such as tetanus toxoid. The conjugates of the present invention overcome this serious limitation in combination vaccine compositions.

BRIEF DESCRIPTION OF THE FIGURES

FIGS. 5A–5H depict tables showing serum antibody of Sprague Dawley rats immunized with Hib-TT, Hib-rPorB and Hib-rP2 measured by ELISA.

FIGS. 6A and 6B depict data showing PRP-specific ELISA IgG response in rats for Hib conjugate vaccines with different carrier proteins. Two different Hib-rPorB preparations were tested (−1 and −2). FIG. 6A is a graphical depiction of the tabular data shown in FIG. 6B.

DETAILED DESCRIPTION OF THE INVENTION

Figure 1:
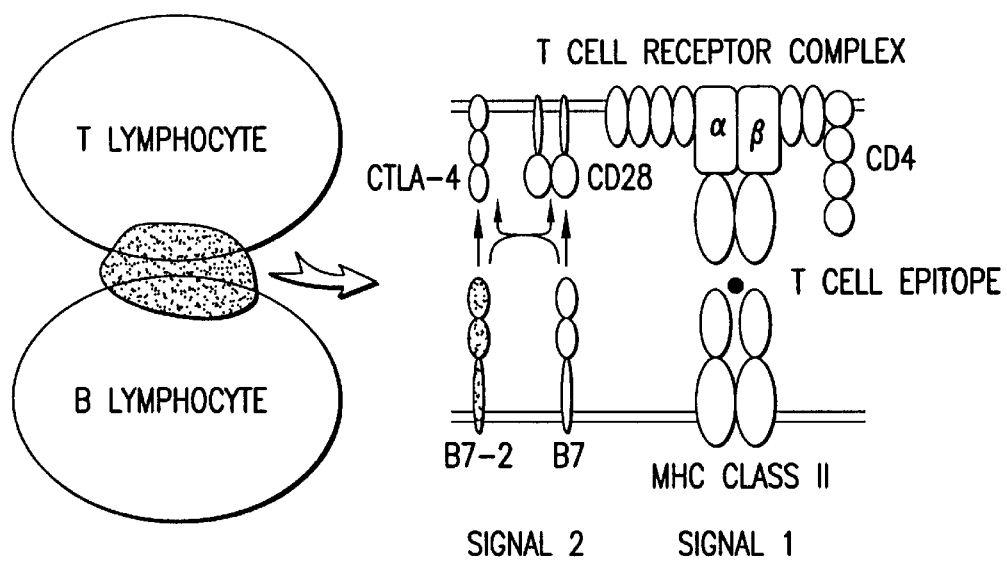
FIG. 1 depicts a graphical representation of T-lymphocyte costimulation.

The present invention relates to a vaccine for inducing an immune response in an animal comprising the outer membrane meningococcal group B porin protein linked to Hib polysaccharide, together with a pharmaceutically acceptable diluent, carrier, or excipient, wherein the vaccine may be administered in an amount effective to elicit an immune response in an animal to *H. influenzae*. In a preferred embodiment, the animal is a mammal selected from the group consisting of humans, cattle, pigs, sheep, and chickens. In another preferred embodiment, the mammal is a human.

By the term "rPorB" is intended the mature, refolded class 2 or class 3 outer membrane protein from *N. meningitidis* and fusions thereof comprising amino acids 1 to 20 or 1 to 22 of the T7 gene φ10 capsid protein. Methods for high level expression of the mature class 2 and class 3 rPorB and fusions thereof, refolding, and purification are described in (47) and U.S. Pat. No. 5,439,808, the disclosures of which are incorporated herein by reference. The recombinant porin may be expressed at high levels from *E. coli* according to U.S. Pat. No. 5,439,808, or from yeast according to Ser. No. 08/792,302. In a preferred embodiment, the class 3 rPorB is expressed from the host BL21(DE3)ΔompA which has been transformed with the gene coding for the rPorB, is substantially pure and is refolded according to U.S. Pat. No. 5,439,808.

The *H. influenzae* capsular polysaccharide can be isolated according to methods well known to those of ordinary skill in the art. See, Schneerson et al. *J. Exp. Med.* 152:361–376 (1980); Marburg et al. *J. Am. Chem. Soc.* 108:5282 (1986); Jennings et al., *J. Immunol.* 127:1011–1018(1981); and Beuvery et al., *Infect. Immunol.* 40:39–45 (1983). In a preferred embodiment, the organism is cultured, the culture supernatant is microfiltered, and the filtrate is passed through a 300,000 molecular weight cut off filter. The permeate is then concentrated, for example, with a 100,000 molecular weight cut off filter. This 100,000–300,000 molecular weight material is then oxidized with a mild oxidant such as metaperiodate, the product filtered through a 30,000 molecular weight filter and then concentrated with a 5,000 molecular weight filter, to give a polysaccharide having aldehyde groups that may be used directly for conjugation. The preferred polysaccharide has a molecular weight of about 5,000–50,000. A more preferred polysaccharide has a molecular weight of about 10,000–50,000, however other molecular weight ranges may be employed as desired.

It will be understood by those of skill in the art that the capsular polysaccharide-protein carrier conjugates of the vaccine may be produced by several different methods. The types of covalent bonds which couple a polysaccharide to a protein carrier, and the means of producing them, are well known to those of skill in the art. Details concerning the chemical means by which the two moieties can be linked may be found in U.S. Pat. Nos. 5,623,057, 5,371,197, 5,192,540,4,902,506 and 4,356,170, the contents of which are herein incorporated by reference in their entirety. For a review, see *Contributions to Microbiology and Immunology*, vol 10, *Conjugate Vaccines*, volume editors J. M. Cruse and R. E. Lewis, Jr., 1989, and (29). One such method is the reductive amination process described in Schwartz and Gray (*Arch. Biochim. Biophys.* 181:542–549 (1977)). This process involves producing the polysaccharide in a form which has reducing end groups, and reacting the capsular polysaccharide and rPorB in the presence of cyanoborohydride ions, or another reducing agent. The reducing groups may be formed by selective hydrolysis or specific oxidative cleavage, or a combination of both.

The vaccine of the present invention comprises the Hib-rPor conjugate, in an amount effective depending on the route of administration. Although subcutaneous or intramuscular routes of administration are preferred, the meningococcal group B porin protein, fusion protein or vaccine of the present invention can also be administered by an intraperitoneal, intravenous, or intranasal route. One skilled in the art will appreciate that the amounts to be administered for any particular treatment protocol can be readily determined without undue experimentation. Suitable amounts are expected to fall within the range of 5 to 50 μg per animal, more preferably, about 10 μg per animal.

The vaccine of the present invention may be employed in such forms as capsules, liquid solutions, suspensions or elixirs for oral administration, or sterile liquid forms such as solutions or suspensions. Any inert carrier is preferably used, such as saline, phosphate-buffered saline, or any such carrier in which the conjugate vaccine has suitable solubility properties. The vaccines may be in the form of single dose preparations or in multi-dose flasks which can be used for mass vaccination programs. Reference is made to *Remington's Pharmaceutical Sciences*, Mack Publishing Co., Easton, Pa., Osol (ed.) (1980); and *New Trends and Developments in Vaccines*, Voller et al. (eds.), University Park Press, Baltimore, Md. (1978), for methods of preparing and using vaccines.

The vaccines of the present invention may further comprise adjuvants which enhance production of *H. influenzae*-specific antibodies. Such adjuvants include, but are not limited to, various oil formulations such as Freund's complete adjuvant (CFA), stearyl tyrosine (ST, see U.S. Pat. No. 4,258,029), the dipeptide known as MDP, saponin, aluminum hydroxide, and lymphatic cytokine.

Freund's adjuvant is an emulsion of mineral oil and water which is mixed with the immunogenic substance. Although Freund's adjuvant is powerful, it is usually not administered to humans. Instead, the adjuvant alum (aluminum hydroxide) or ST may be used for administration to a human. The conjugate vaccine may be absorbed onto the aluminum hydroxide from which it is slowly released after injection. The conjugate vaccine may also be encapsulated within liposomes according to Fullerton, U.S. Pat. No. 4,235,877.

In another preferred embodiment, the conjugate of the invention is combined with other immunogens that are used to vaccinate animals. Thus, the conjugate of the invention may be combined with DTaP or DTaP IPV for administration to the animal. DTaP is a combination vaccine for diphtheria, tetanus, and acellular pertussis, which is available from Amvax, Inc., Beltsville, Md. In a preferred embodiment, the acellular pertussis is in an oxidized form as is available from Amvax, Inc.

In another preferred embodiment, the present invention relates to a method of inducing an immune response in an animal comprising administering to the animal the vaccine of the invention in an amount effective to induce an immune response. Optionally, the vaccine of the invention may be coadministered with effective amounts of other immunogens as mentioned above to generate multiple immune responses in the animal.

The following examples are illustrative, but not limiting, of the methods and compositions of the present invention. Other suitable modifications and adaptations of the variety of conditions and parameters normally encountered in this art which are obvious to those skilled in the art are within the spirit and scope of the present invention.

EXAMPLES

Example 1 rPorB Expression, Isolation, Refolding, and Purification

Bacterial strains, growth conditions, and reagents—Genomic DNA was isolated from Group B *N. meningitidis* strain 44/176 (serotype 15) employing standard procedures and used as a polymerase chain reaction template for amplification of the class 3 protein gene as described elsewhere (47). The amplified product was cloned into NdeI and XhoI sites of the pET17b plasmid (Novagen, Inc.) that was used to transform competent *E. coli* DH5α. Plasmid DNA from selected DH5α clones was isolated and employed to transform *E. coli* BL21 [DE3]-ΔompA. The transformants were selected by carbenicillin and expression induced by the addition of IPTG to a final concentration of 0.4 mm.

Overexpression of rPorB in *E. coli* and refolding purification procedures.

The levels of rPorB protein expressed at various times after induction were monitored by subjecting the cell extracts to SDS-PAGE in 8–16% gradient gels, using a Novex® system (Novel Experimental Technology, San Diego, Calif.) followed by Comassie brilliant blue staining, and densitometric analysis using a IS-1000 Digital Imaining System® (Innotech Scientific Corp. San Leandro, Calif.). The overexpressed rPorB was isolated by resuspending and lysing the bacterial cells with a Stansted air-driven cell disrupter (Stansted Fluid Power Ltd.) in TEN buffer (50 mm Tris-HCl, 1 mm EDTA, 100 mm NaCl, pH 8.0) followed by centrifugation and isolation of the pellet containing rPorB aggregated in the form of inclusion bodies (IBs). After washing the pellet with 0.5% deoxycholate in TEN buffer, followed by two rinses with TEN buffer, the protein was solubilized by resuspending and sonicating the IBs in freshly prepared 8 M urea solution for 5 min using a water bath sonicator. Refolding of rPorB into its native conformation was achieved by employing a detergent-assisted refolding procedure. Equal volumes of urea-dissolved IBs and 10% Zwittergent® 3, 14 (Calbiochem-Behring Corp.) were combined and the final porin extract applied to a Sephacryl® S-300 (5×100 cm) column (Pharmacia Fine Chemicals, Inc.) equilibrated in a buffer comprised of 100 mm Tris-HCl, 200 mm NaCl, 10 mm EDTA, 20 mm $CaCl_2$, and 0.05% Zwittergent® 3, 14, pH 8.0. Fractions containing rPorB were identified by SDS-PAGE, pooled, and applied to Hiload® Q-Sepharose® HP ion exchange (2.6×20 cm) column (Pharmacia) equilibrated in 25 mm Tris-HCl, 200 mm NaCl, 1.0 mm EDTA, and 0.05% Z 3–14 pH 8.0. A gradient of 0.2–1.0 mm NaCl was applied and rPorB eluted as a single peak. Protein concentration was estimated by measuring the absorbance at 280 nm, employing a HP Model 8453 UV/Vis rapid scan spectrophotometer equipped with a diode array detector (Hewlett-Packard Company, Palo Alto, Calif.), using amolar extinction coefficient of 41,960 which was calculated based on PorB aromatic amino acid content according to Mach et al. (42).

Example 2

PRP Polysacchaide Production, Purification and Oxidation

Figure 2:
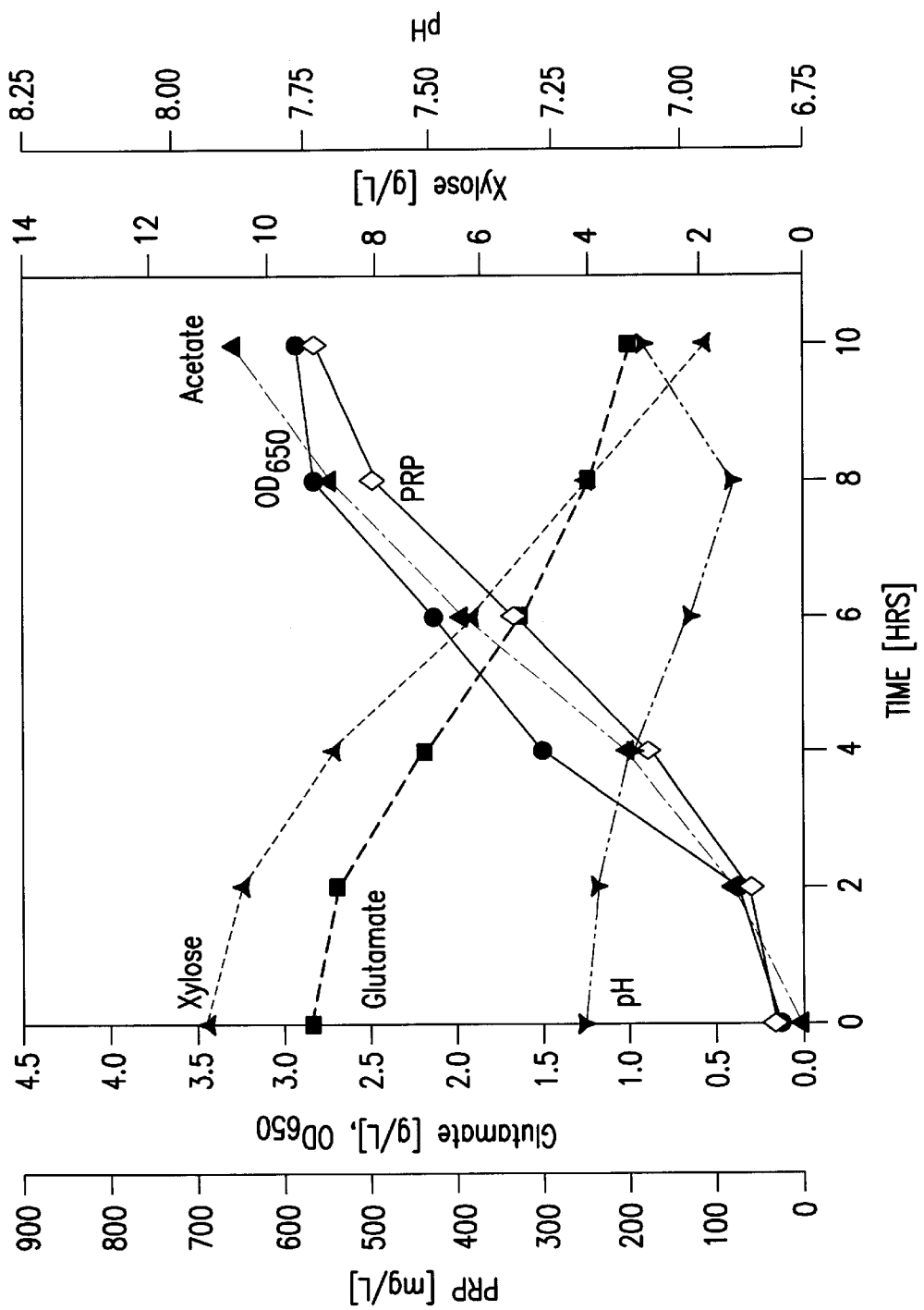
FIG. 2 depicts a graph showing B1HB1030 fermentation profile.

A 14 L fermentation of *H. influenzae* type b was performed using MAE II media as follows. *H. influenzae* type b strain Eagan was obtained in a 4 mL seed culture vial from the Ultra Low liquid nitrogen freezer and thawed at room temperature for thirty minutes. A 250 mL shake flask with 50 mL of MME II medium (10 mg/L hemin) was inoculated with 1 mL of seed culture to produce seed I (SI). The SI flask was incubated for 10 hours at 37° C. and 150 RPM in a shaker incubator (Innova® 4330, New Brunswick Scientific Co., Inc.). Twelve mL of S1 were used to inoculate 600 mL of MME II (10 mg/1-hemin) in a 2.8 L Fernbach flask to produce S11. The S11 flask was incubated for 9 hours at 37° C. and 150 RPM in a shaker incubator. Six hundred mL (4% (v/v) inoculum) of S11 culture were used to inoculate 13.4 L of MMEII (10 g/L xylose, 10 mg/L hemin) in a 20 L BIOFLO IV fermentor (New Brunswick Scientific Co., Inc.). An example of the fermentation profile is shown in FIG. 2. After 10 h of the fermentation, harvesting by microfiltration was initiated, using a hollow fiber cartridge with a 0.2 μm pore size rating with a 0.14 $m^2$ surface area made out of polysulfone (Milipore). The permeate was sterile filtered into a 20 L carboy and the carboy was placed at 2–8° C. until further processed. The filtrate was then processed through a 300,000 molecular weight cut off (MWCO) filter (Milipore) and the permeate retained. This permeate was then applied to a 100,000 (MWCO) filter (Milipore) and concentrated to greater than 20 mg/ml. The retentate was oxidized at 25° C. for 2 h with sodium metaperiodate. The oxidized PRP was ultra filtrated through a 30,000 MWCO filter (Milipore) and the permeate retained. This permeate was then applied to a 5,000 MWCO filter (Milipore), concentrated to a final concentration of greater than 90 mg/ml, diafiltrated against DI water, and lyophilized.

Example 3

PRP-PorB Conjugate Preparation

Figure 3:
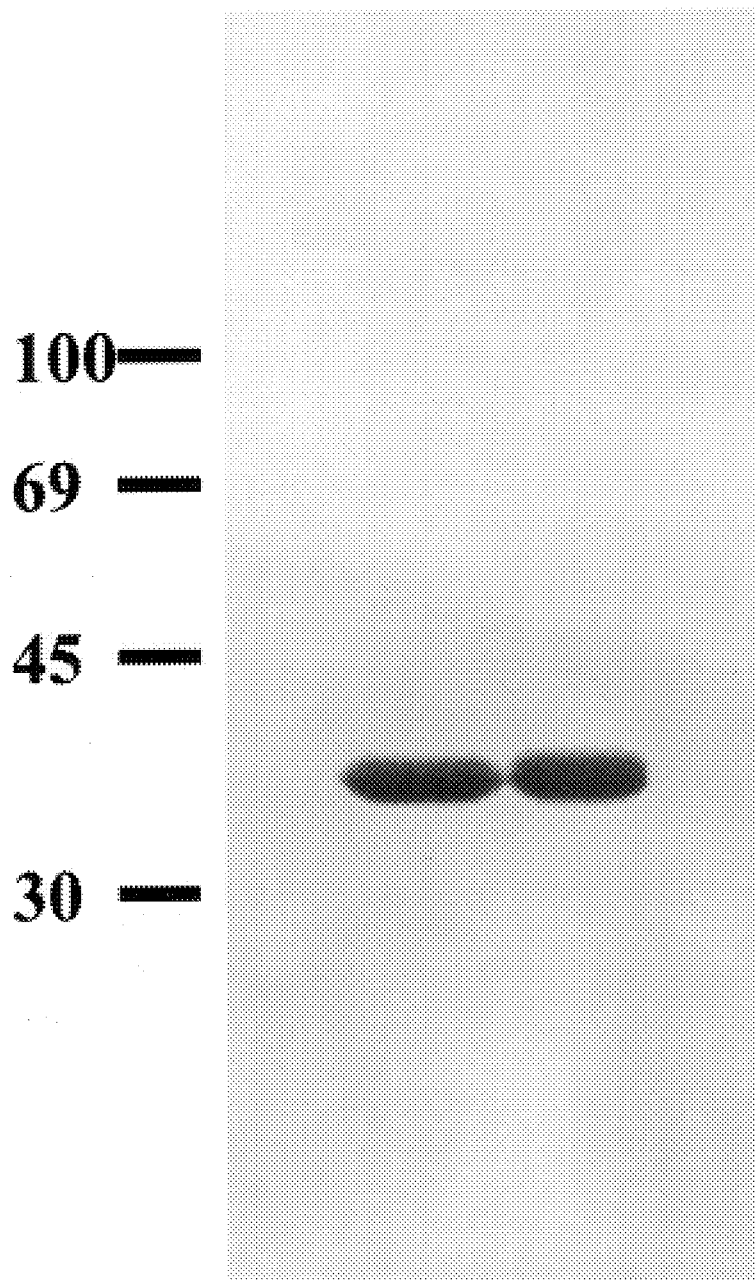
FIG. 3 depicts a stained SDS-PAGE gel of the purified rPorB used for conjugation.
Figure 4:
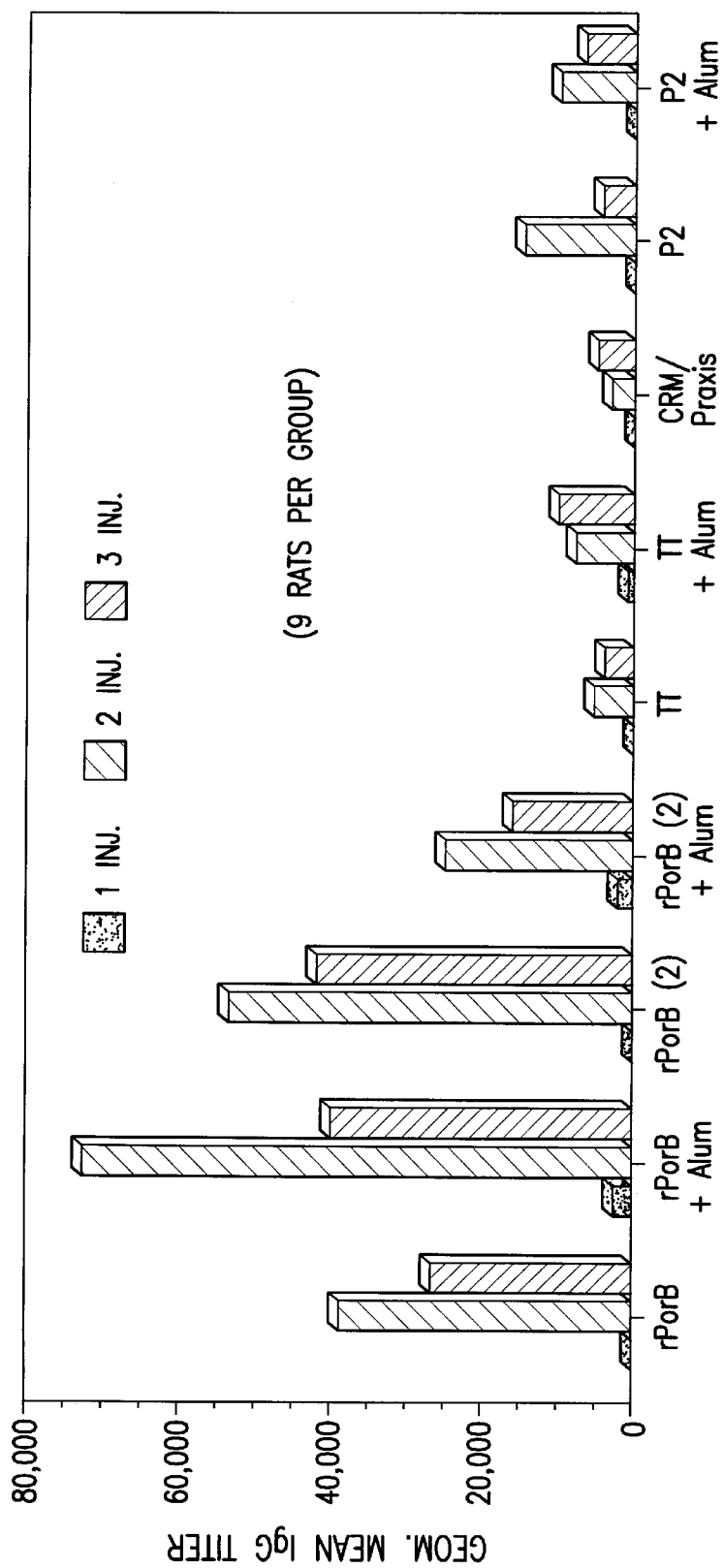
FIG. 4 depicts a bar graph showing the Hib polysaccharide-specific IgG response in rats for Hib conjugates with various carrier proteins.

The purified rPorB used for conjugation is shown in FIG. 3. The previously described oxidized PRP polysaccharide was added to a rPorB solution (at 10 mg/ml concentration in 0.25 M HEPES, 0.2 M NaCl, and 0.05% Zwittergent® 3,14 of pH 8.5) to make a 10 mg/ml polysaccharide solution. The solution was mixed for 1 min after which sodium cyanoborohydride was added to a final concentration of 6 mg/ml. The solution was then placed in a water bath at 28–30° C. for 16 to 24 h. The conjugation reaction was stopped by the addition of 2 M ethanolamine solution at pH 8.5 and incubated at 28 to 30° C. for additional an 16 to 24 hours. The reaction mixture was then applied to a Superdex® 200 prep Grade column (Pharmacia) preequilibrated and run with PBS containing 0.01% thimerosal. The fractions eluting in the void volume of this column as monitored by UV-280 nm absorbance were collected, pooled, and stored at 4° C. prior to their analysis. Two chemical analysis were preformed to assess the PRP content (orcinol/ferric chloride/hydrochloric acid assay (50)) and the rPorB content (Coomassie protein assay (5)).

Example 4

Evaluation of the PRP-rPorB Conjugate in Rats

Female Sprague-Dawley rats (4–6 weeks old) in groups of ten were injected subcutaneously with 10 µg of conjugated PRP in 0.5 ml of PBS containing 0.01% thimerosal, either unabsorbed or preabsorbed on aluminum hydroxide (Alhydrogel®, Superfos Export Co. A/S Denmark,) (final elemental aluminum concentration of 1 mg/ml) at days 0, 28, and 49. Bleeds were performed at day 0, 28, 38, 49, and the animals exsanquinated at day 59.

Serum antibody measurement by ELISA. The human serum albumin (HSA) (Sigma, St. Louis, Mo.) conjugates used for ELISA assays were prepared by reductive amination as previously described. The oxidized PRP polysaccharide was added to HSA followed by reduction with $NaBH_3CN$ as described (28). The conjugates were isolated by gel filtration chromatography, and stored freeze-dried at −70° C. PRP-specific antibody titers were determined by an enzyme-linked immunosorbent assay (ELISA). Polystyrene, 96-well, flat-bottom microtiter plates (NUNC Polysorb®) (Nunc, Naperville, Ill.) were coated with PRP-HSA conjugates in PBS (0.01 M sodium phosphate, 0.15 M NaCl, pH 7.4) at 0.25 µg/well (100 µl/well) by incubating for 1 hour at 37° C., followed by a PBS-Tween® Co. 0.5% (v/v) Tween® 20 in PBS) wash (5 times). All subsequent incubations were conducted at room temperature. PBS-Tween® was used for all required washes. The coated plates were then blocked with PBS and 0.1% (w/v) Carnation nonfat dry milk for IgM ELISAs at 0.15 ml/well for 1 hour, followed by a wash. Sera were diluted 2-fold, in duplicate, in the plate at 100 µl/well and incubated for 1 hour, followed by a wash. Antibody conjugate (peroxidase-labelled goat anti-rat (Kirkegaard & Perry Lab. Gaithersburg, Md.) was added at 100 µl/well and incubated for 30 minutes, followed by a wash. A 1:1 dye and substrate solution (Kirkegaard & Perry TMB and peroxide) was added at 0.05 ml/well and incubated for 10 minutes. The peroxidase reaction was then stopped with 1M $H_3PO_4$ at 0.05 ml/well, and the plate was read on a Molecular Devices Emax® microplate reader (Molecular Devices, Corp., Sunnyvale, Calif.) at a wavelength of 450 nm, using 650 nm as a reference wavelength. Background absorbances were determined in several no-serum control wells and averaged for each plate. For each serum dilution, the average background absorbance was subtracted, and then duplicate serum absorbance values were averaged. A modified Scatchard plot was used for the subsequent data analysis, where the absorbance (y-axis) was plotted against the absorbance times the reciprocal dilution (x-axis) (18,22). Under conditions allowing equilibrium and antibody excess, a straight line was obtained for each serum dilution series; this line was extrapolated to the x-axis for the determination of an antibody titer. A positive control serum, with a previously determined antibody titer, was used on each plate in order to provide a reference to which all sera were standardized, minimizing plate-to-plate and day-to-day variations. The results of these assays, comparing the PorB-PRP conjugate (with and without alum) with conjugates constructed from tetanus toxoid, CRM, are shown in FIGS. 4 and 5A–5G.

Example 5

Comparisons of Hib-rPorB, Hib-TT and Two Commericially Available Hib Vaccines

Immuno-stimulatory effects of two preparations of the Hib-rPorB conjugate (Hib-rPorB-1 and Hib-rPorB-2), the Hib-TT (tetanus toxoid) conjugate, and two commercially available vaccines, HbOC from Lederle Laboratories, Division of American Cyanamide Company, Pearl River, N.Y., (CRM carrier), and PRP-T from Connaught Laboratories, Inc., Swiftwater, Pa. (tetanus toxoid carrier), were compared.

Figure 6A:
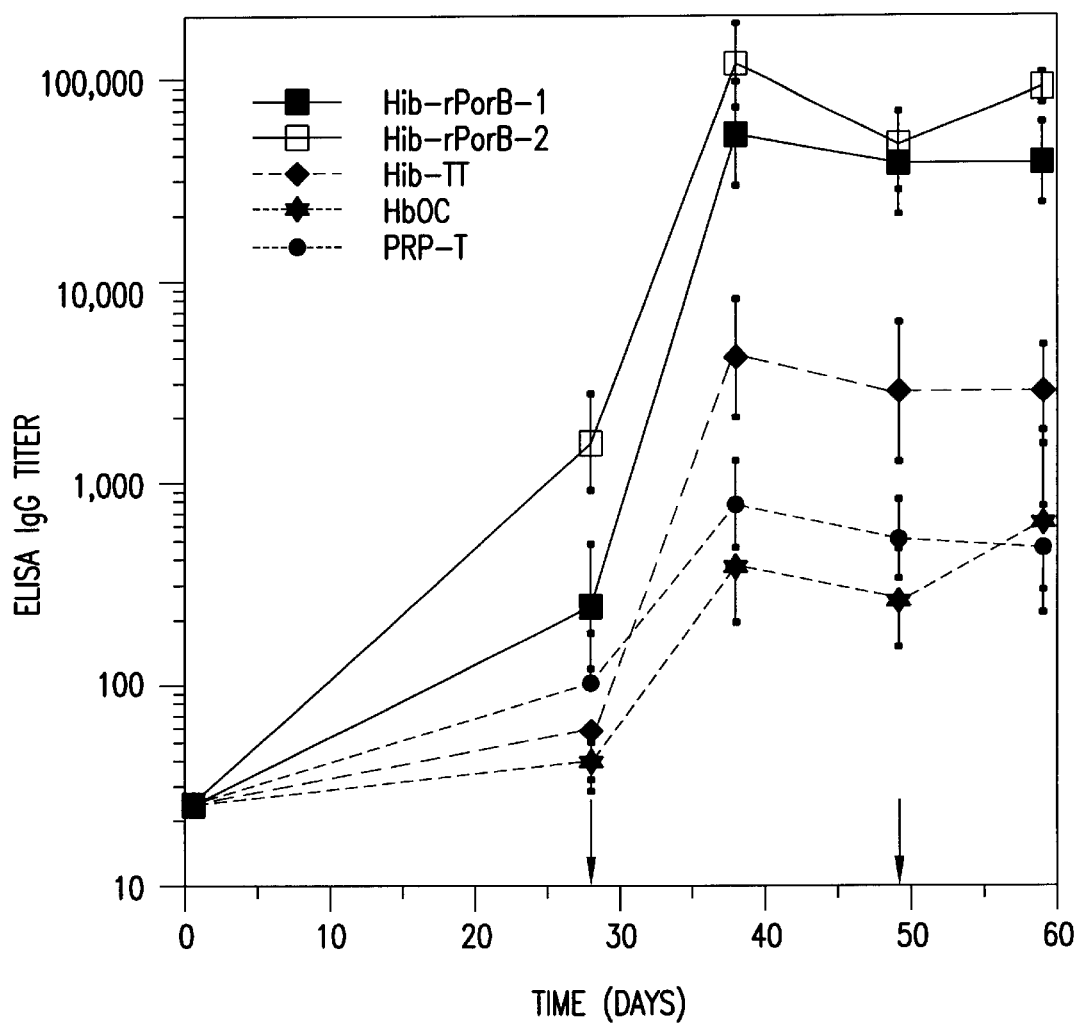

Rats (4–6 weeks old) were immunized with conjugated PRP doses of 10 ∞g at 1, 28 and 49 days. In addition to pre-immune samples, serum samples were taken at 28, 38, 49 and 59 days. Results are shown in FIGS. 6A and 6B. The ELISA IgG titer refers to anti-polysaccharide antibodies.

Figure 7:
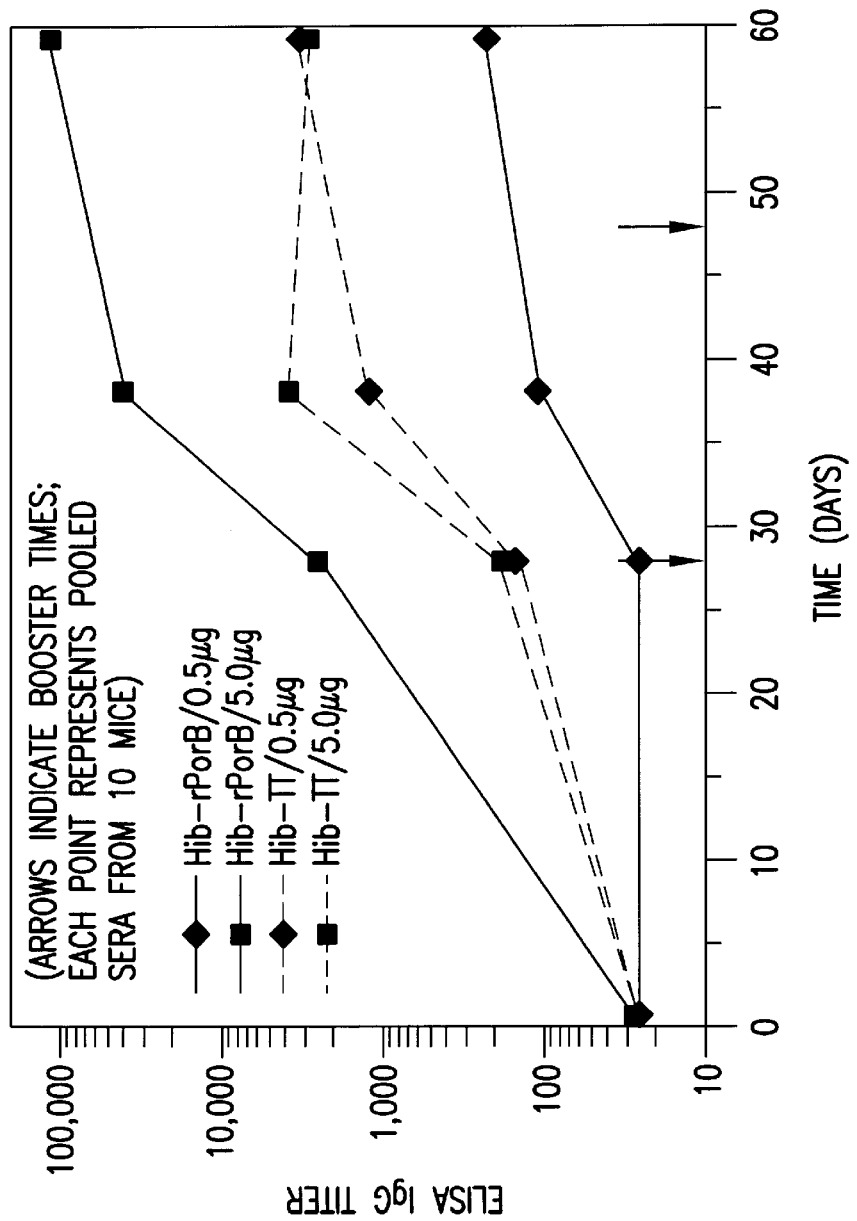
FIG. 7 depicts a graph showing polysaccharide-specific IgG elicited by Hib conjugate vaccines in CD-1 mice.

The graphic depiction of the data in FIG. 6A shows that the Hib-rPorB conjugates produced a response at least two orders of magnitude greater than that of the other conjugate vaccines. FIG. 6B shows corresponding tabulated data. "Responders" are defined as exhibiting IgG ELISA titers greater than or equal to 4-fold above pre-immune, where all pre-immune values were <50 and adjusted to 25 for calculations. Similar experiments comparing Hib-TT, Hib-rPorB-1, and Hib-rPorB-2 were performed in mice using conjugate dosages of 5.0 µg and 0.5 µg. The data is shown in FIG. 7.

Figure 8:
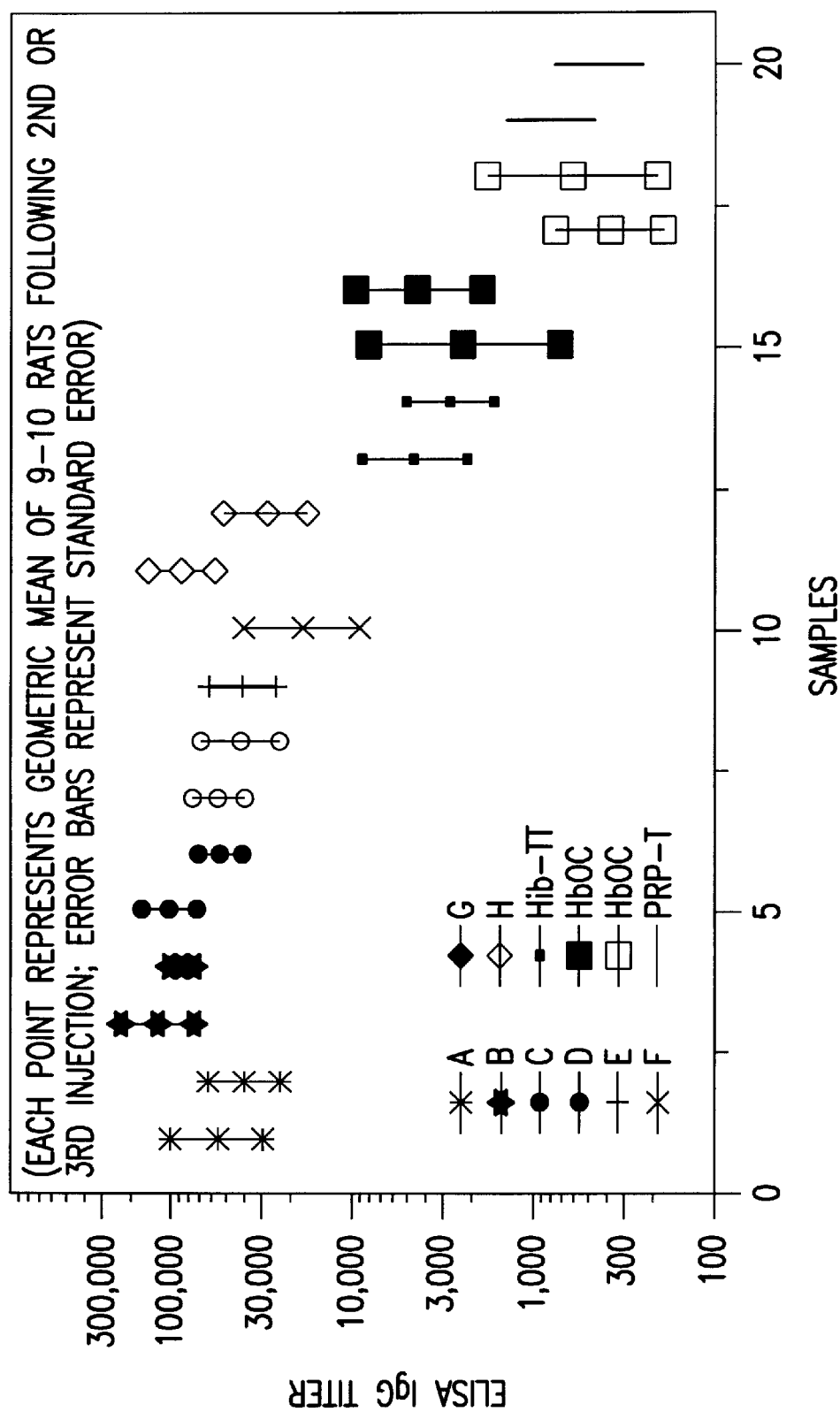
FIG. 8 depicts a graph showing polysaccharide-specific IgG elicited by Hib conjugate vaccines in rats.

Finally, eight different preparations of Hib-rPorB (A-H in FIG. 8) were compared to Hib-TT and Hib-CRM conjugates. Hib-rPorB preparations were consistently two orders of magnitude more stimulatory than the Hib-TT or Hib-CRM conjugates, as shown by ELISA assay of anti-polysaccharide IgG antibodies in rats. This data is shown in FIG. 8.

Having now fully described this invention, it will be understood by those of ordinary skill in the art that the invention can be practiced within a wide and equivalent range of conditions, formulations and other parameters without affecting the scope of the invention or any embodiment thereof. All patents, patent applications and publications cited herein are fully incorporated by reference herein in their entirety.

REFERENCES

1. Azuma, M., M. Cayabyab, D. Buck, J. H. Phillips and L. L. Lanier. 1992. CD28 interaction with B7 costimulates primary allogeneic proliferative responses and cytotoxicity mediated by small, resting T lymphocytes. J.Exp.Med. 175:353–360.

2. Azuma, M., D. Ito, H. Yagita, et al. 1993. B70 antigen is a second ligand for CTLA-4 and CD28. Nature 366:76–79.

3. Baskar, S., S. Ostrand-Rosenberg, N. Nabavi, L. M. Nadler, G. J. Freeman and L. H. Glimcher. 1993. Constitutive expression of B7 restores immunogenicity of tumor cells expressing truncated major histocompatibility complex class II molecules. Proc.Natl.Acad.Sci.USA 90:5687–5690.

4. Blake, M. S. and E. C. Gotschlich. 1986. Functional and immunological properties of pathogenic neisserial surface proteins. p. 377–400. In: M. Inouye, Bacterial Outer Membranes as Model Systems. John Wiley, New York.

5. Bradford, M. M. 1976. A Rapid and sensitive method for the quantitation of microgram quantities of protein utilizing the principle of protein-dye binding. Analyt.Biochem. 72:248–254.

6. Butcher, S., M. Sarvas and K. Runeberg-Nyman. 1991. Class-3 porin protein of *Neisseria meningitidis*: Cloning and structure of the gene. Gene 105:125–128.

7. Carbonetti, N. H. and P. F. Sparling. 1987. Molecular cloning and chracterization of the structural gene for protein I, the major outer membrane protein of *Neisseria gonorrhoeae*. Proc.Nat.Acad.Sci.USA. 84:9084–9088.

8. Chen, L., S. Ashe, W. A. Brady, et al. 1992. Costimulation of antitumor immunity by the B7 counterreceptor for the T lymphocyte molecules CD28 and CTLA-4. Cell 71:1093–1102.

9. Connell, T. D., D. Shaffer and J. G. Cannon. 1990. Characterization of the repertoire of hypervariable regions in the protein II (opa) gene family of *Neisseria gonorrhoeae*, Molec.Microbiol. 4:439–449.

10. Donnelly, J. J., R. R. Deck and M. A. Liu. 1990. Immunogenicity of a *Haemophilus influenzae* polysaccharide-*Neisseria meningitidis* outer membrane protein complex conjugate vaccine. J.Immunol. 145:3071–3079.

11. Falkow, S., 1997. What is a pathogen? ASM News 63:359–365.

12. Freeman, G. J., F. Borriello, R. J. Iodes, et al. 1993. Uncovering of functional alternative CTLA-4 counter-receptor in B7-deficient mice. Science 262:907–909.

13. Freeman, G. J., F. Borrielo, R. J. Hodes, et al. 1993. Murine B7-2, an alternative CTLA4 counter-receptor that costimulates T cell proliferation and interleukin-2 production. J.Exp.Med. 178:2185–2192.

14. Freeman, G. J., A. S. Freedman, J. M. Segil, G. Lee, J. F. Whitman and L. M. Nadler. 1989. B7, a new member of the Ig superfamily with unique expression on activated and neoplastic B cells. J.Immunol. 143:2714–2722.

15. Freeman, G. J., G. S. Gray, C. D. Gimmi, et al. 1991. Structure, expression, and T cell costimulatory activity of the murine homologue of the human B lymphocyte activation antigen B7. J.Exp.Med. 174:625–631.

16. Freeman, G. J., J. G. Gribben, V. A. Boussiotis, et al. 1993. Cloning of B7-2: a CTLA-4 counter-receptor that costimulates human T cell proliferation. Science 262:909–911.

17. Freeman, G. J., D. B. Lombard, C. D. Gimmi, et al. 1992. CTLA-4 and CD28 nRNA are coexpressed in most T cells after activation. Expression of CTLA-4 and CD28 mRNA does not correlate with the pattern of lymphokine production. J. Immunol. 149:3795–3801.

18. Fusco, P. C., 1983. Studies on *Escherichia coli* somatic pili: Phenotypic expression, serological specificity, and physicochemical characterization. Ph.D. Thesis, University of Pittsburgh, Pittsburgh, Pa.

19. Gimmi, C. D., G. J. Freeman, J. G. Gribben, G. Gray and L. M. Nadler. 1993. Human T-cell clonal anergy is induced by antigen presentation in the absence of B7 costimulation. Proc.Natl.Acad.Sci.USA 90:6586–6590.

20. Gimmi, C. D., G. J. Freeman, J. G. Gribben, et al. 1991. B-cell surface antigen B7 provides a costimulatory signal that induces T cells to proliferate and secrete interleukin 2. Proc.Natl.Acad.Sci.USA 88:6575–6579.

21. Gotscblich, E. C., M. E. Seiff, M. S. Blake and J. M. Koomey. 1987. Porin protein of Neisseria gonorrhoeae: cloning and gene structure. Proc.Nat.Acad.Sci.USA. 84:8135–8139.

22. Hanson, M. S. and C. C. Brinton, Jr., 1988. Identification and characterization of the Escherichia coli type 1 pilus tip adhesion protein. Nature 332:265–268.

23. Harper, K, C. Balzano, E. Rouvier, M. G. Mattei, M. F. Luciani and P. Golstein. 1991. CTLA4 and CD28 activated lymphocyte molecules are closely related in both mouse and human as to sequence, message expression, gene structure, and chromosomal location. J.Immunol. 147:1037–1044.

24. Hathcock, K. S., G. Laszlo, H. B. Dickter, J. Bradshaw, P. S. Linsley and R. J. Hodes. 1993. Identification of an alternative CTLA-4 ligand costimulatory for T cell activation. Science 262:905–907.

25. Janeway, C. A., Jr. and K Bottomly. 1994. Signals and signs for lymphocyte responses. Cell 76:275–285.

26. Jeanteur, D., J. H. Lakely and F. Pattus. 1991. The bacterial porin superfamily: sequence alignment and structure prediction. Molec.Microbiol. 5:2153–2164.

27. Jenkins, M. K. and J. G. Johnson. 1993. Molecules involved in T-cell costimulation. Curr.Opin.Immunol. 5:361–367.

28. Jennings, H. J., A. Gamian, F. Michon and F. E. Ashton. 1989. Unique intermolecular bactericidal epitope involving the homosialopolysaccharide capsule on the cell surface of group B Neisseria meningitidis and Escherichia coli K1. J. Immunol. 142:3585–3591.

29. Jennings, H. J. and R. K. Sood. 1994. Synthetic glycoconjugates ashumanvaccines. p.325–371. In: Y. C. Lee and R. T. Lee, Neoglycoconjugates: Preparation and applications. Academic Press, New York.

30. June, C. H., J. A. Bluestone, L. M. Nadler and C. B. Thompson. 1994. The B7 and CD28 receptor families. Immunol.Today 15:321–331.

31. Lindsten, T., K. P. Lee, E. S. Harris, et al. 1993. Characterization of CTLA-4 structure and expression on human T cells. J. Immunol. 151:3489–3499.

32. Linsley, P. S., W. Brady, L. Grosmaire, A. Aruffo, N. K. Damle and J. A. Ledbetter. 1991. Binding of the B cell activation antigen B7 to CD28 costimulates T cell proliferation and interleukin 2 mRNA accumulation. J.Exp.Med. 173:721–730.

33. Linsley, P. S., W. Brady, M. Urnes, L. S. Grosmaire, N. K. Damle and J. A. Ledbetter. 1991. CTLA-4 is a second receptor for the B cell activation antigen B7. J.Exp.Med. 174:561–569.

34. Linsley, P. S., E. A. Clark and J. A. Ledbetter. 1990. T-cell antigen CD28 mediates adhesion with B cells by interacting with activation antigen B7/BB-1. Proc.Natl.Acad.Sci.USA 87:5031–5035.

35. Liu, M. A., A. Friedman, A. I. Oliff, et al. 1992. A vaccine carrier derived from Neisseria meningitidis with mitogenic activity for lymphocytes. Proc.Natl.Acad.Sci.USA 89:4633–4637.

36. Livingston, P. O., 1993. Approaches to augmenting the IgG antibody response to melanoma ganglioside vaccines. Ann.N.Y.Acad.Sci. 690:204–213.

37. Livingston, P. O., M. J. Calves, F. Helling, W. D. Zollinger, M. S. Blake and G. H. Lowell. 1993. GD3/proteosome vaccines induce consistent IgM antibodies against the ganglioside GD3. Vaccine 11:1199–1204.

38. Lowell, G. H., 1990. Proteosomes, hydrophobic anchors, iscoms, and liposomes for improved presentation of peptides and protein vaccines. p. 141–160. In: G. C. Woodrow and M. M. Levine, New Generation Vaccines. Marcel Dekker, Inc., New York.

39. Lowell, G. H., W. R. Ballou, L. F. Smith, R. A. Wirtz, W. D. Zollinger and W. T. Hockmeyer. 1988. Proteosome-lipopeptide vaccines: enhancement of immunogenicity for malaria CS peptides. Science 240:800–802.

40. Lowell, G. H., L. F. Smith, R. C. Seid and W. D. Zollinger. 1988. Peptides bound to proteosomes via hydrophobic feet become highly immunogenic without adjuvant. J.Exp.Med. 167:658–663.

41. Lynch, E. C., M. S. Blake, E. C. Gotschlich and A. Mauro. 1984. Studies of porins: Spontaneously transferred from whole cells and reconstituted from purified proteins of *Neisseria gonorrhoeae* and *Neisseria meningitidis*. Biophys.J. 45:104–107.

42. Mach, H., C. R. Middaugh and R. V. Lewis. 1992. Statistical determination of the average values of the extinction coefficients of tryptophan and tyrosine in native proteins. Anal.Biochem. 200:74–80.

43. Mauro, A., M. S. Blake and P. Labarca. 1988. Voltage gating of conductance in lipid bilayers induced by porin from outer membranes of Neisseria gonorrhoeae. Proc.Nat.Acad.Sci.USA. 85:1071–1075.

44. Melancon, J., R. A. Murgita and I. W. DeVoe. 1983. Activation of murine B lymphocytes by Neisseria meningitidis and isolated meningococcal surface antigens. Infect.Immun. 42:471–479.

45. Mueller, D. L., M. K. Jenkins and R. H. Schwartz. 1989. Clonal expansion versus functional clonal inactivation: a costimulatory signalling pathway determines the outcome of T cell antigen receptor occupancy. Annu.Rev.Immunol. 7:445–480.

46. Norton, S. D., L. Zuckerman, K. B. Urdahl, R. Shefner, J. Miller and M. K. Jenkins. 1992. The CD28 ligand, B7, enhances IL-2 production by providing a costimulatory signal to T cells. J.Immunol. 149:1556–1561.

47. Qi, H. L., J. Y. Tai and M. S. Blake. 1994. Expression of large amounts of Neisserial porin proteins in *Escherichia coli* and refolding of the proteins into native trimers. Infect.Immun. 62:2432–2439.

48. Razi-Wolf, Z., G. J. Freeman, F. Galvin, B. Benacerraf, L. Nadler and H. Reiser. 1992. Expression and finction of the murine B7 antigen, the major costimulatory molecule expressed by peritoneal exudate cells. Proc.Natl.Acad.Sci.USA 89:4210–4214.

49. Reiser, H., G. J., Freeman, Z. Razi-Wolf, C. D. Gimmi, B. Benacerraf and L. M. Nadler. 1992. Murine B7 antigen provides an efficient costimulatory signal for activation of murine T lymphocytes via the T-cell receptor/CD3 complex. Proc.Natl.Acad.Sci.USA 89:271–275.

50. Reuter, G. and R. Schauer. 1994. Determination of sialic acids. p. 168–199. In: W. J. Lennarz and G. W. Hart, Methods in Enzymology Vol. 230 Techniques in Glycobiology. Academic Press, New York.

51. Schwartz, R. H. 1992. Costimulation of T lymphocytes: The role of CD28, CTLA-4, and B7/BB1 in interleukin-2 production and immunotherapy. Cell 71:1065–1068.

52. Sparkes, B. G., 1983. Immunomodulating activity of meningococcal antigens. Can.J.Microbiol. 29:1611–1618.

53. Sparkes, B. G., 1983. Dual effect of meningococcal antigens on a T cell dependent immune response. Can.J.Microbiol. 29:1619–1625.

54. Tan, P., C. Anasetti, J. A. Hansen, et al. 1993. Induction of alloantigen-specific hyporesponsiveness in human T lymphocytes by blocking interaction of CD28 with its natural ligand B7/BB1. J.Exp.Med. 177:165–173.

55. Townsend, S. E. and J. P. Allison. 1993. Tumor rejection after direct costimulation of CD8+T cells by B7-transfected melanoma cells. Science 259:368–370.

56. Ulmer, J. B., C. J. Burke, C. Shi, A. Friedman, J. J. Donnelly and M. A. Liu. 1992. Pore formation and mitogenicity in blood cells by the class 2 protein of *Neisseria meningitidis*. J.Biol.Chem. 267:19266–19271.

57. Vordermeier, H. and W. G. Bessler. 1987. Polyclonal activation of murine B lymphocytes in vitro by *Salmonella typhimurium* porins. Immunobiol. 175:245–251.

58. Vordermeier, H., H. Drexler and W. G. Bessler. 1987. Polyclonal activation of human peripheral blood lymphocytes by bacterial porins and defined porin fragments. Immunol.Lett. 15:121–126.

59. Ward, M. J., P. R. Lambden and J. E. Heckels. 1992. Sequence analysis and relationships between meningococcal class 3 serotype proteins and other porins from pathogenic and non-pathogenic Neisseria species. FEMS Microbiol.Lett. 73:283–289.

60. Wetzler, L. M., M. S. Blake, K. Barry and E. C. Gotschlich. 1992. Gonococcal porin vaccine evaluation: comparison of Por proteosomes, liposomes, and blebs isolated from rmp deletion mutants. J.Infect.Dis. 166:551–555.

61. White, R. G., 1976. The adjuvant effect of microbial products on the immune response. Ann.Rev.Microbiol. 30:579–595.

62. Young, J. D. E., M. S. Blake, A. Mauro and Z. A. Cohn. 1983. Properties of the major outer membrane protein from *Neisseria gonorrhoeae* incorporated into model lipid membranes. Proc.Natl.Acad.Sci.USA 80:3831–3835.

What is claimed is:

1. An *H. influenzae* type b (Hib) polysaccharide-substantially pure, refolded meningococcal outer membrane protein (rPorB) conjugate.

2. The conjugate of claim 1, wherein said polysaccharide has a molecular weight range of 5,000 to 50,000.

3. The conjugate of claim 1, wherein said conjugate is obtained by reductive amination of a Hib polysaccharide and rPorB, wherein the Hib polysaccharide has been oxidized or selectively hydrolyzed to give aldehyde groups.

4. The conjugate of claim 1, wherein said conjugate is obtained by reductive amination of a Hib Polysaccharide and rPorB, wherein the Hib polysaccharide has been oxidized to give aldehyde groups.

5. The conjugate of any of one claims 1–4, wherein said rPorB is a class 3 rPorB.

6. An Hib polysaccharide-rPorB conjugate obtained according to a method, comprising:
 (a) obtaining a Hib polysaccharide;
 (b) oxidizing or selectively hydrolyzing said polysaccharide to generate aldehyde groups;
 (c) obtaining a rPorB; and
 (d) conjugating the polysaccharide containing aldehyde groups to the rPorB by reductive amination.

7. The conjugate of claim 6, wherein said Hib polysaccharide is oxidized and has a molecular weight range of 5,000 to 50,000.

8. The conjugate of claim 6, wherein said rPorB is a class 3 rPorB.

9. A pharmaceutical composition comprising the conjugate of claim 1 or 6 and a pharmaceutically acceptable carrier.

* * * * *